US00PP23660P2

(12) United States Plant Patent
Dümmen

(10) Patent No.: US PP23,660 P2
(45) Date of Patent: Jun. 11, 2013

(54) ***VERBENA* PLANT NAMED 'DUEMPFLAWI'**

(50) Latin Name: *Verbena hybrida*
Varietal Denomination: Duempflawi

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 23 days.

(21) Appl. No.: 13/317,915

(22) Filed: Oct. 31, 2011

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — C. A. Whealy

(57) ABSTRACT

A new and distinct cultivar of *Verbena* plant named 'Duempflawi', characterized by its semi-upright and mounded plant habit; freely branching habit; freely flowering habit; and large white-colored flowers that are held above and beyond the foliar plane in mounded umbels.

1 Drawing Sheet

Botanical designation: *Verbena hybrida.*
Cultivar denomination: 'DUEMPFLAWI'.

BACKGROUND OF THE INVENTION

The present invention relates to a new and distinct cultivar of *Verbena* plant, botanically known as *Verbena hybrida* and hereinafter referred to by the name 'Duempflawi'.

The new *Verbena* plant is a product of a planned breeding program conducted by the Inventor in Rheinberg, Germany. The objective of the breeding program is to create new semi-upright *Verbena* plants with numerous large and attractive flowers.

The new *Verbena* plant originated from a cross-pollination made by the Inventor in July, 2008 in Rheinberg, Germany of a proprietary selection of *Verbena hybrida* identified as code number F-01-23-9, not patented, as the female, or seed, parent with a proprietary selection of *Verbena hybrida* identified as code number V06-3920-001, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2010.

Asexual reproduction of the new *Verbena* plant by terminal cuttings in a controlled greenhouse environment in Rheinberg, Germany since June, 2010 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duempflawi'. These characteristics in combination distinguish 'Duempflawi' as a new and distinct *Verbena* plant:

1. Semi-upright and mounded plant habit.
2. Freely branching habit.
3. Freely flowering habit.
4. Large white-colored flowers that are held above and beyond the foliar plane in mounded umbels.

Plants of the new *Verbena* differ from plants of the female parent selection primarily in plant habit as plants of the new *Verbena* are more upright than plants of the female parent selection. In addition, plants of the new *Verbena* have larger flowers than plants of the female parent selection.

Plants of the new *Verbena* differ from plants of the male parent selection primarily in branching habit as plants of the new *Verbena* are more freely branching than plants of the male parent selection. In addition, plants of the new *Verbena* have whiter-colored flowers than plants of the male parent selection.

Plants of the new *Verbena* can be compared to plants of the *Verbena hybrida* 'Sunmaririho', U.S. application Ser. No. 09/859,545, now abandoned. In side-by-side comparisons conducted in Rheinberg, Germany, plants of the new *Verbena* differed from plants of 'Sunmaririho' in the following characteristics:

1. Plants of the new *Verbena* were more upright than plants of 'Sunmaririho'.
2. Plants of the new *Verbena* had shorter internodes than plants of 'Sunmaririho'.
3. Plants of the new *Verbena* had smaller leaves than plants of 'Sunmaririho'.
4. Plants of the new *Verbena* had larger flowers than plants of 'Sunmaririho'.
5. Plants of the new *Verbena* had shorter peduncles than plants of 'Sunmaririho'.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant. The photograph is a side perspective view of a typical flowering plant of 'Duempflawi'.

DETAILED BOTANICAL DESCRIPTION

The aforementioned photograph and following observations, measurements and values describe plants grown in 12-cm containers during the summer in a glass-covered greenhouse in Rheinberg, Germany and under cultural practices which closely approximate commercial *Verbena* production. During the production of the plants, day and night temperatures averaged 18° C. and light levels averaged 4,500 lux. Plants were pinched one time about three weeks after planting and were ten weeks old when the photograph and the description were taken. In the description, color references are made to The Royal Horticultural Society Colour Chart, 1995 Edition, except where general terms of ordinary dictionary significance are used.

Botanical classification: *Verbena hybrida* 'Duempflawi'.

Parentage:

*Female, or seed, parent*.—Proprietary selection of *Verbena hybrida* identified as code number F-01-23-9, not patented.

*Male, or pollen, parent*.—Proprietary selection of *Verbena hybrida* identified as code number V06-3920-001, not patented.

Propagation:

*Type*.—Terminal cuttings.

*Time to initiate roots, summer*.—About five days at about 20° C.

*Time to initiate roots, winter*.—About seven days at about 20° C.

*Time to produce a rooted young plant, summer*.—About three weeks at about 20° C.

*Time to produce a rooted young plant, winter*.—About four weeks at about 20° C.

*Root description*.—Fine, fibrous; white in color.

*Rooting habit*.—Freely branching; dense.

Plant description:

*Plant habit*.—Semi-upright and mounded plant habit; freely branching habit with about three to six primary lateral branches with secondary lateral branches potentially forming at every node; pinching enhances lateral branch development; dense and bushy plant habit; moderately vigorous growth habit.

*Plant height*.—About 16 cm.

*Plant diameter*.—About 22 cm.

Lateral branch description:

*Length*.—About 18 cm.

*Diameter*.—About 2.5 mm.

*Internode length*.—About 3 cm.

*Texture*.—Pubescent.

*Strength*.—Strong.

*Color*.—Close to 146B.

Foliage description:

*Arrangement*.—Opposite, simple.

*Length*.—About 3.6 cm.

*Width*.—About 2 cm.

*Shape*.—Lanceolate.

*Apex*.—Acute.

*Base*.—Attenuate.

*Margin*.—Lobed.

*Texture, upper and lower surfaces*.—Pubescent, coarse.

*Venation pattern*.—Pinnate.

*Color*.—Developing and fully expanded leaves, upper surface: Close to 147A; venation, close to 147A. Developing and fully expanded leaves, lower surface: Close to 147B; venation, close to 147C.

*Petioles*.—Length: About 3 mm. Diameter: About 1.5 mm. Texture, upper and lower surfaces: Smooth, glabrous. Color, upper and lower surfaces: Close to 144B.

Flower description:

*Flower arrangement and habit*.—Salverform flowers arranged in hemispherical terminal umbels; umbels dense and mounding; numerous umbels covering the entire plant; flowers face upward or outwardly; freely flowering habit with about 14 to 20 flowers and flower buds per inflorescence.

*Fragrance*.—None detected.

*Natural flowering season*.—Plants flower continuously from the spring through the fall in Germany; plants begin flowering about eight weeks after planting.

*Flower longevity*.—Individual flowers last about one week on the plant; flowers persistent.

*Flower buds*.—Length: About 1.9 cm. Diameter: About 5 mm. Shape: Oval to tubular. Color: Close to 155A.

*Inflorescence size*.—Height: About 2.8 cm. Diameter: About 6.5 cm.

*Flowers*.—Appearance: Flared trumpet, corolla fused, five-parted. Diameter: About 2.5 cm. Depth: About 2.3 cm.

*Corolla*.—Arrangement: Single whorl of five fused petals. Petal lobe length: About 1.2 cm. Petal lobe width: About 1.1 cm. Petal lobe shape: Obovate. Petal lobe apex: Emarginate. Petal margin: Entire. Petal texture, upper and lower surfaces: Smooth, glabrous. Color: When opening, upper surface: Close to 155A. When opening, lower surface: Close to 155B. Fully opened, upper and lower surfaces: Close to 155C.

*Calyx*.—Arrangement: Star-shaped calyx with five fused sepals. Sepal length: About 1.4 cm. Sepal width: About 0.8 mm. Sepal shape: Ligulate. Sepal apex: Acute. Sepal margin: Entire. Sepal texture, upper and lower surfaces: Pubescent, coarse. Sepal color, upper surface: Close to 144B to 144C. Sepal color, lower surface: Close to 146B and 144C.

*Peduncles*.—Length: About 4.5 cm. Diameter: About 2.2 mm. Strength: Strong. Texture: Pubescent. Color: Close to 144A.

*Pedicels*.—Length: About 0.5 mm. Diameter: About 0.5 mm. Strength: Strong. Texture: Smooth, glabrous. Color: Close to 144A.

*Reproductive organs*.—Stamens: Quantity and arrangement: About four to five per flower, adnate to corolla tube. Anther shape: Oval. Anther length: About 0.7 mm. Anther color: Close to 7D. Pollen amount: Moderate. Pollen color: Close to 2D. Pistils: Quantity: One per flower. Pistil length: About 1.8 cm. Stigma shape:

Bi-parted. Stigma color: Close to 144B. Style length: About 1.7 cm. Style color: Close to 144A. Ovary color: Close to 144B. Fruits and seeds: Fruit and seed development has not been observed on plants of the new *Verbena*.

Temperature tolerance: Plants of the new *Verbena* have been observed to tolerate temperatures from about 5° C. to about 40° C.

Pathogen/pest resistance: Plants of the new *Verbena* have not been observed to be resistant to pathogens and pests common to *Verbena* plants.

It is claimed:

1. A new and distinct *Verbena* plant named 'Duempflawi' as illustrated and described.

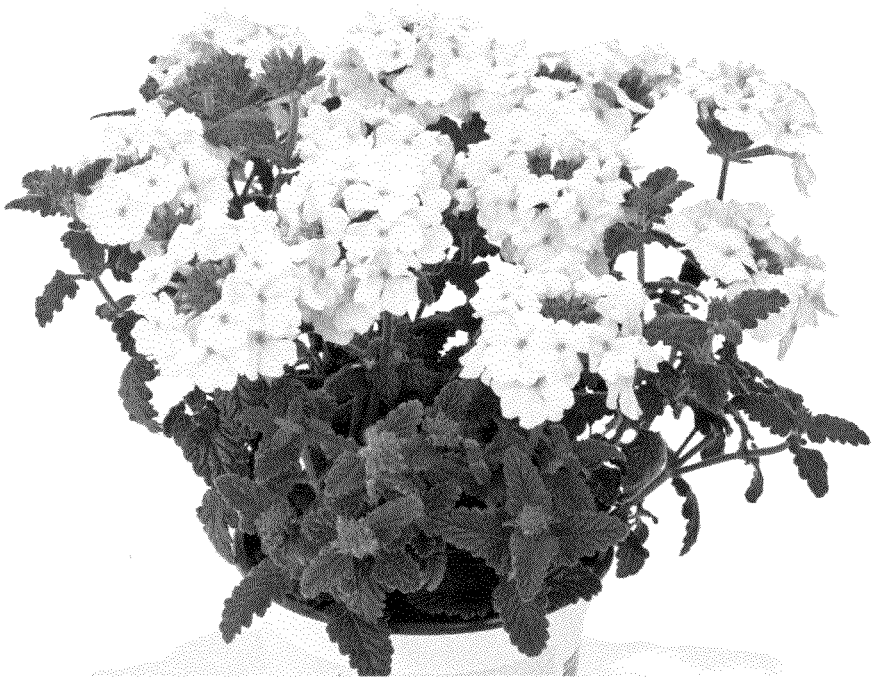

* * * * *